(12) United States Patent
Ealick et al.

(10) Patent No.: US 7,037,718 B2
(45) Date of Patent: May 2, 2006

(54) MUTANT PURINE NUCLEOSIDE PHOSPHORYLASE PROTEINS AND CELLULAR DELIVERY THEREOF

(75) Inventors: Steven E. Ealick, Ithaca, NY (US); William B. Parker, Birmingham, AL (US); John A. Secrist, III, Birmingham, AL (US); Eric J. Sorscher, Birmingham, AL (US)

(73) Assignees: Cornell Research Foundation, Inc., Ithaca, NY (US); Southern Research Institute, Birmingham, AL (US); The UAB Research Foundation, Birmingham, AL (US)

( * ) Notice: Subject to any disclaimer, the term of this patent is extended or adjusted under 35 U.S.C. 154(b) by 494 days.

(21) Appl. No.: 10/035,300

(22) Filed: Oct. 26, 2001

(65) Prior Publication Data

US 2003/0228576 A1    Dec. 11, 2003

(51) Int. Cl.
 *C12N 15/85* (2006.01)
(52) U.S. Cl. .................. 435/325; 435/252.3; 536/23.1; 514/44
(58) Field of Classification Search ................. 435/325, 435/252.3; 536/23.1; 514/44
See application file for complete search history.

(56) References Cited

U.S. PATENT DOCUMENTS 5,552,311 A    9/1996  Sorscher et al. .......... 435/240.2

FOREIGN PATENT DOCUMENTS

| EP | 0 392 745 B1 | 10/1990 |
|---|---|---|
| EP | 0 415 731 A2 | 3/1991 |
| WO | PCT/US96/10250 | 6/1996 |
| WO | WO 96/40238 | 12/1996 |

OTHER PUBLICATIONS

Maynes, JT et al. Design of an adenosine phosphorylase by active site modification of murine purine nucleoside phosphorylase. Biochemical Journal, 1999, vol. 344, pp. 585-592.*
Anderson (2001) Editorial Excitement in Gene Therapy! Human Gene Therapy, vol. 12, pp. 1483-1484.
Andreansky et al. (1996) The application of genetically engineered herpes simplex viruses to the treatment of experimental brain tumors Proc. Natl. Acad. Sci. USA, vol. 93, pp. 11313-11318.
Beck et al. (1995) The Thymidine Kinase/Ganciclovir-Mediated "Suicide" Effect is Variable in Different Tumor Cells Human Gene Therapy, vol. 6, pp. 1525-1530.
Bischoff et al. (1996) An Adenovirus Mutant That Replicates Selectively in p53-Deficient Human Tumor Cells Science, vol. 274, pp. 373-376.

Cacciapuoti et al. (1994) Purification and Characterization of Extremely Thermophilic and Thermostable 5'-Methylthioadenosine Phosphorylase from the Archaeon *Sulfolobus solfataricus* The Journal of Biological Chemistry, vol. 269, No. 40, pp. 24762-24769.
Cacciapuoti et al. (1996) Extremely thermophilic and thermostable 5'-methylthioadenosine phosphory from the archaeon *Sulfolobus solfataricus* Gene Cloning and amino acid sequence determination Eur. J. Biochem., vol. 239, pp. 632-637.
Dilber et al. (1997) Gap Junctions Promoe the Bystander Effect of Herpes Simplex Virus Thymidine Kinase *in Vivo* Cancer Research, No. 57, pp. 1523-1528.
Dix et al. (2001) Minireview: Does the Antitumor Adenovirus ONYX-015/d11520 Selectively Target Cells Defect in the p53 Pathway? Journal of Virology, pp. 5443-5447.
Doronin et al. (2001) Tissue-Specific, Tumor-Selective, Replication-Competent Adenovirus Vector for Cancer Gene Therapy Journal of Virology, pp. 3314-3324.
Elshami et al. (1996) Gap junctions play a role in the 'bystander effect' of the herpes simplex virus thymidine kinase/ganciclovir system in vitro Gene Therapy 3, pp. 85-92.
Freeman et al. (1993) The "Bystander Effect": Tumor Regression When a Fraction of the Tumor Mass is Genetically Modified Cancer Research 53, pp. 5274-5283.
GE et al. (1997) Transduction of Cytosine Deaminase Gene Makes Rat Glioma Cells Highly Sensitive to 5-Fluorocytosine Int. J. Cancer, No. 71, pp. 675-679.
Gnant et al. (1999) Systemic Administration of a Recombinant Vaccinia Virus Expressing the Cytosine Deaminase Gene and Subsequent Treatment with 5-Fluorocytosine Leads to Tumor-specific Gene Expression and Prolongation of Survival in Mice Cancer Research 59, pp. 3396-3403.

(Continued)

*Primary Examiner*—Anne-Marie Falk
*Assistant Examiner*—Jon Eric Angell
(74) *Attorney, Agent, or Firm*—Gifford, Krass, Groh, Sprinkle, Anderson & Citkowski, P.C.

(57) ABSTRACT

The present invention provides a procaryotic host cell stably transformed or transfected by a vector including a DNA sequence encoding for mutant purine nucleoside phosphorylase or hydrolase. The transformed or transfected procaryotic host cell can be used in combination with a purine substrate to treat tumor cells and/or virally infected cells. The present invention provides nucleotide sequences encoding mutant *E. coli* derived purine nucleoside phosphorylase proteins which can be used in conjunction with an appropriate substrate to produce toxins which impair abnormal cell growth. The invention provides for delivery of the toxin by generation within target cells or by administration and delivery to the cells from without.

9 Claims, No Drawings

OTHER PUBLICATIONS

Hall et al. (1998) p53-dependent cell death/apoptosis is required for a productive adenovirus infection Nature Medicine, vol. 4, No. 9, pp. 1068-1072.

Heise et al. (1997) ONYX-015, and EIB gene-attenuated adenovirus, causes tumor-specific cytolysis and antitumoral efficacy that can be augmented by standard chemotherapeutic agents Nature Medicine, vol. 3, No. 6, pp. 639-645.

Heise et al. (1999) Intravenous Administration of ONYX-015, a Selectively Replicating Adenovirus, Induces Antitumoral Efficacy Cancer Research 59, pp. 2623-2628.

Huang et al. (1987) Phosphorolytic Cleavage of 2-Fluoroadenine from 9-$\beta$-D-Arabinofuranosyl-2-Fluoroadenine by *Escherichia Coli* A Pathway for 2-Fluoro-Atp Production Biochemical Pharmarology, vol. 30, No. 18, pp. 2945-2950.

Huber et al. (1994) Metabolism of 5-fluorouracil in human colorectal tumor cells transduced with the cytosine deaminase gene: Significant antitumor effects when only a small percentage of tumor cells express cytosine deaminase Proc. Natl. Acad. Sci. USA, vol. 91, pp. 8302-8306.

Imaizumi et al. (1998) Bystander Tumoricidal Effect and Gap Junctional Communication in Lung Cancer Cell Lines American Journal of Respiratory Cell and Molecular Biology,vol. 18, No. 2, pp. 205-212.

Jaffe (1975) Nucleoside Analogs as Antiparasitic Agents Annals of the New York Acamdemy of Sciences, Chemistry, Biology, and Clinical Uses of Nucleoside Analogs, vol. 255, pp. 306-316.

Johnson et al. (2002) Selectively replicating adenoviruses targeting deregulated E2F activity are potent, systemic antitumor agents Cancer Cell, vol. 1, pp. 325-337.

Khuri et al. (2000) A controlled trial of intratumoral ONYXA-015, a selectively-replicating adenovirus, in combination with cisplating and 5-fluorouracil in patients with recurrent head and neck cancer Nature Medicine, vol. 6, No. 8, pp. 879-885.

Lane (1998) Killing tumor cells with viruses-a question of specificity Nature Medicine, vol. 4, No. 9,, pp. 1012-1013.

Lemmon et al. (1997) Anaerobic bacteria as a gene delivery system that is controlled by the tumor microenvironment Gene Therapy 4, pp. 791-796.

Linke (1998) Has the smart bomb been diffused? Nature, vol. 395, pp. 13 and 15.

Lowe (1997) Progress of the smart bomb cancer virus. A mutant adenovirus capable of preferentially destroying cancer cells shows promise in preclinical studies (639-645), Nature Medicine, vol. 3, No. 6, pp. 606-607.

Ma et al. (2002) Cells Designed to Delivery Anticancer Drugs by Apoptosis Cancer Research 62, pp. 1382-1387.

Nemunaitis et al. (2001) Phase II Trial of Intratumoral Administrative on ONY-015, a Replication-Selective Adenovirus, in Patients With Refractory head and Neck Cancer Journal of Clinical Oncology, vol. 19, No. 2, pp. 289-298.

Nemunaitis et al. (2001) Intravenous infusion of a replication-selective adenovirus (ONYX-015) in cancer patients: safety, feasability and biological activity, Gene Therapy, Abstract, 2 pages.

Pennisi (1998) Training Viruses to Attack Cancers Coffey et al. (1998) Reovirus Therapy of Tumors with Activatred Ras Pathway Science, vol. 282, pp. 1244-1246 and 1332-1334.

Ram et al. (1993) *In Situ* Retroviral-mediated Gene Transfer for the Treatment of Brain Tumors in Rats Cancer Research 53, pp. 83-88.

Rothmann et al. (1998) Replication of ONYX-015, a Potential Anticancer Adenovirus, is Independent of p53 Status in Tumor Cells Journal of Virology, vol. 72, pp. 9470-9478.

Sacco et al. (1996) Partial regression,yet incomplete eradication of mammary tumors in transgenic mice by retrovirally mediated HSVtk transfer 'in vivo' Gene Therapy 3, pp. 1151-1156.

Searle et al. (1998) Adenoviral vectors: not to be sneezed at Gene Therapy 5, pp. 725-727.

Shinoura et al. (1999) Highly Augmented Cytopathic Effect of a Fiber-mutant EIB-defective Adenovirus for Gene Therapy of Gliomas Cancer Research 59, pp. 3411-3416.

Wildner et al. (1999) Therapy of Colon Cancer with Oncolytic Adenovirus is Enhanced by the Additionof Herpes Simplex Virus-*thymidine kinase* Cancer Research 59, pp. 410-413.

Yeh et al. (1997) Advances in adenoviral vectors: from genetic engineering to their biology the FASEB Journal, vol. 11, pp. 615-623.

Allen (1989) Stealth™ Liposomes: Avoiding Retinculoendothelial Uptake Liposomes in the Therapy of Infectious Diseases and Cancer, pp. 405-415.

Barankiewicz and Jezewska (1975) Inosine-Guanosine and Adenosine Phosphorylase Activities in Hepatopancreas of *Helix pomatia* (Gastropoda) Comp. Biochem. Physiol., vol. 54B, pp. 239-242.

Bennett et al. (1984) Mode of Action of 2-amino-6-chloro-1-deazapurine Biochemical Pharmacology, vol. 33, No. 2, pp. 261-271.

Bohman et al. (1983) Mechanism of Cytostatic Action of Novel 5-(Thien-2-yl) and 5-(Furan-2-yl)-Substituted Pyrimidine Nucleoside Analogues Against Tumor Cells Transfected by the Thymidine Kinase Gene of Herpes Simplex Virus The Journal of Biological Chemistry, vol. 269, No. 11, pp. 8036-8043.

Brockman et al. (1980) Metabolism and Chemotherapeutic Activity of 9-$\beta$-D-Arabinofuranysyl-2-fluoroadenine against Murine Leukemia L1210 and Evidence for Its Phosphorylation by Deoxycytidine Kinase Cancer Research, 40:3610-3615.

Burland et al. (1995) Analysis of the *Escherichia coli* Genome VI: DNA Sequence of the Region From 92.8 Through 100 Minutes Nucleic Acids Research, vol. 23, No. 12, pp. 2105-2119.

Carson et al. (1980) Deoxycytidine Kinase-Mediated Toxicity of Deoxyadenosine Analogs Toward Malignant Human Lymphoblasts *in vitro* and Toward Murine L1210 Leukemia *in vivo* Proc. Natl. Acad. Sci. USA, vol. 77, No. 11, pp. 6865-6869.

Connors (1995) The Choice of Prodrugs for Gene Directed Enzyme Prodrug Therapy of Cancer Gene Therapy, 2:702-709.

Cook et al. (1985) Crystallization and Preliminary X-ray Investigation of Purine-nucleoside Phosphorylase from *Escherichia coli* The Journal of Biological Chemistry, vol. 260, No. 24, Issue of Oct. 25, pp. 12968-12969.

Culver and Blease (1994) Gene Therapy for Cancer Trends in Genetics, 10:174-178.

Da Costa et al. (1996) Converting Cancer Genes into Killer Genes Proc. Natl. Acad. Sci. USA, 93:4192-4196.

Daddona et al. (1986) Expression of Human Malaria Parasite Purine Nucleoside Phosphorylase in Host Enzyme-deficient Erythrocyte Culture The Journal of Biological Chemistry, vol. 261, Issue of Sep. 5, pp. 11667-11673.

Dewey and Kidder (1973) Partial Purification and Properties of a Nucleoside Hydrolase from *Crithidia* Archives of Biochemistry and Biophysics, 157:380-387.

Dykes et al. (1992) Development of Human Tumor Xenograft Models for *in vivo* Evaluation of New Antitumor Drugs Contri. Oncol. Basel, Karger, 42:1-22.

Ealick et al. (1990) Three-dimensional Structure of Human Erythrocytic Purine Nucleoside Phosphorylase at 3.2 Å Resolution The Journal of Biological Chemistry, vol. 265, No. 3, Issue of Jan. 25, pp. 1812-1820.

Freeman et al. (1996) *In situ* Use of Suicide Genes for Cancer Therapy Seminars in Oncology, 23:31-45.

Freireich et al. (1966) Quantitative Comparison of Toxicity of Anticancer Agents in Mouse, Rat, Hamster, Dog, Monkey and Man Cancer Chemotherapy Reports, vol. 50, No. 4, pp. 219-244.

Gadi et al. (2000) *In vivo* Sensitization of Ovarian Tumors to Chemotherapy by Expression of *E.coli* Purine Nucleoside Phosphorylase in a Samall Fraction of Cells Gene Therapy, 7:1738-1743.

Garver et al. (1994) Strategy for Achieving Selective Killing of Carcinomas Gene Therapy I, 46-50.

Gay (1984) Construction and Characterization of an *Escherichia coli* Strain with a *uncl* Mutation J. Bacteriol, 158:820-825.

Ghoda et al. (1988) Substrate Specificities of 5'-deoxy-5'-methylthioadenosine Phosphorylase from *Trypanosoma brucei brucei* and Mammalian Cells Molecular and Biochemical Parasitology, 27:109-118.

Giebel et al. (1991) Organization and Nucleotide Sequences of the Human Tyrosinase Gene and a Truncated Tyrosinase-Related Segment Genomics, 9:435-445.

Gutteridge and Davies (1981) Enzymes of Purine Salvage in *Trypanosoma cruzi* FEBS Letters, vol. 127, No. 2, pp. 21-24.

Hatanka et al. (1975) Adenine Formation from Adenosine by Mycoplasmas: Adenosine Phosphorylase Activity Proc. natl. Acad. Sci. USA, 77:1401-1405.

Hershfield et al. (1991) Use f Site-Directed Mutagenesis to Enhance the Epitope-Shielding Effect of Covalent Modification of Proteins with Polyethylene Glycol Proc. Natl. Acad. Sci. USA, 88:7185-7189.

Heyworth et al. (1982) Purine Metabolism in *Trichomonas vaginalis* FEBS Letters, vol. 1, No. 1, pp. 106-110.

Hughes et al. (1995) Bystander Killing of Melanoma Cells Using the Human Tyrosinase Promoter to Express the *Escherichia coli* Purine Nucleoside Phosphorylase Gene Cancer Research, 55:3339-3345.

Hughes et al. (1998) Cell to Cell Contact is not Required for Bystander Cell Killing by *Escherichia coli* Purine Nucleoside Phosphorylase The Journal of Biological Chemistry, vol. 273, No. 4, Issue of Jan. 23, pp. 2322-2328.

Jensen (1978) Two Purine Nucleoside Phosphorylases in *Bacillus subtilis*. Purification and Some Properties of the Adenosine-Specific Phosphorylase Biochemical et Biophysics Acta, 525:346-356.

Jensen and Nygaard (1975) Purine Nucleoside Phosphorylase from *Escherichia coli* and *Salmonella typhimurium* Eur. J. Biochem., 51:253-265.

Jenuth and Snyder (1991) Nucleotide Sequence of Murine Purine Nucleoside Phosphorylase cDNA Nucleic Acids Research, vol. 19, No. 7, pp. 1708.

Jiao et al. (1993) Long-Term Correction of Rat Model of Parkinson's Disease by Gene Therapy Nature, 362:450-453.

Kidder et al. (1979) The Purine Phosphoribosyltransferases of *Crithidia fasciculata* J. Parasitol., 64(4), pp. 520-525.

Kikuchi et al. (1989) Characteristic Sequences in the Upstream Region of the Human Tyrosinase Gene Biochemica et Biophysica Acta., 1009:283-286.

Koellner et al. (1998) Crystal Structure of the Ternary Complex of *E.coli* Purine Nucleoside Phosphorylase with Formycin B, a Structural Analogue of the Substrate Inosine, and Phosphate (Sulphate) at 2.1 Å Resolution Journal of Molecular Biology, pp. 153-166.

Kolls et al. (1994) Prolonged and Effective Blockade of Tumor Necrosis Factor Activity Through Adenovirus-mediated Gene Transfer Proc. Natl. Acad. Sci. USA, vol. 91, pp. 215-219.

Königk (1978) Purine Nucleotide Metabolism in Promastigotes of *leishmania tropica*: Inhibitory Effect of Allopurinol and Analogues of Purine Nucleosides. Tropmed. Parasit., 29:435-438.

Koszalka and Krenitsky (1978) Nucleosidases from *Leishmania donovani* The Journal of Biological Chemistry, vol. 254, No. 17, Issue of Sep. 10, pp. 8185-8193.

Krohne et al. (2001) Mechanisms of Cell Death Induced by Suicide Genes Encoding Purine Nucleoside Phosphorylase and Thymidine Kinase in Human Hepatocellular Carcinoma Cells *in vitro* Hepatology, vol. 34, No. 3, pp. 511-518.

Lockett et al. (1997) Relative Efficiency of Tumor Cell Killing *in vitro* by Two Enzyme-prodrug Systems Delivered by Identical Adenovirus Vectors Clinical Caner Research, vol. 3, pp. 2075-2080.

Mao et al.(1997) The Crystal Structure of *Escherichia coli* Purine Nucleoside Phosphorylase: A Comparison with the Human Enzyme Reveals a Conserved Topology Structure, vol. 5, No. 10, pp. 1373-1383.

Martinello-Wilks et al. (1998) *In vivo* Gene Therapy for Prostate Cancer: Preclinical Evaluation of Two Different Enzyme-directed Prodrug Therapy Systems Delivered by Identical Adenovirus Vectors Human Gene Therapy, 9:1617-1626.

Maynes et al. (1999) Design of an Adenosine Phosphorylase by Active-site Modification of Murine Purine Nucleoside Phorphorylase Biochem. J., 344, pp. 585-592.

Maynes et al. (2000) Further Refinement on the Engineering of Adenosine Phosphorylase from Purine Nucleoside Phorphorylase Purine and Pyrimidine Metabolism in Man X, 21, pp. 107-110.

McElwain et al. (1988) *Acholeplasma laidlawii* B-PG9 Adenine-specific Purine Nucleoside Phosphorylase that Accepts Ribose-1-Phosphate, Deoxyribose-1-Phosphate, and Xylose-1-Phosphate Journal of Bacteriology, 170:564-567.

Melton et al. (1999) The Use of Prodrugs in Targeted Anticancer Therapies S.T.P. Pharma Sciences, 9(1), pp. 13-33.

Miech et al. (1975) Pathways of Nucleotide Metabolism in *Schistosoma Mansoni*-VI-Adenosine Phosphorylase Biochemical Pharmacology, 24:407-411.

Miller and Rosman (1989) Improved Retroviral Vectors for Gene Transfer and Expression BioTechniques, 7:980-991.

Mohr et al. (2000) Gene Therapy of Hepatocellular Carcinoma *in vitro* and *in vivo* in Nude Mice by Adenoviral Transfer of the *Escherichia coli* Purine Nucleoside Phosphorylase Gene Hepatology, vol. 31, No. 3, pp. 606-614.

Montgomery and Hewson (1968) Analogs of 6-Methyl-9β-D-ribofuranosylpurine J. Med. Chem., 11:48-52.

Moolten (1994) Drug Sensitivity ("Suicide") Genes for Selective Cancer Chemotherapy Cancer Gene Therapy, 1: 279-287.

Mullen (1994) Metabolic Suicide Genes in Gene Therapy Pharmac. Ther., 63:199-207.

Nelson et al. (1992) Isolation and Expression of a Murine Purine Nucleoside Phosphorylase-encoding cDNA and Sequence Similarity with the Human Message Gene, 113: 215-221.

Nestler et al. (1997) Foamy Virus Vectors for Suicide Gene Therapy Gene Therapy, 4:1270-1277.

Niculescu-Duvaz et al. (1998) Gene-directed Enzyme Prodrug Therapy Bioconjugate Chem., 9:4-22.

Park et al. (1997) Upregulation of Tissue-Specific Suicide Gene Expression in Melanoma Using a Melanocyte-Specific Enhancer Results in Increased Cytotoxicity of the Purine Nucleoside Phosphorylase Gene in Melanoma Human Gene Therapy, 10:889-898.

Park et al. (1999) Augmentation of Melanoma-Specific Gene Expression Using a Tandem Melanocyte-Specific Enhancer Results in Increased Cytotoxicity of the Purine Nucleoside Phosphorylase Gene in Melanoma Human Gene Therapy, 10:889-898.

Parker et al. (1997) In vivo Gene Therapy of Cancer with E.coli Purine Nucleoside Phosphorylase Human Gene Therapy 8:1637-1644.

Parker et al. (1998) Metabolism and Metabolic Actions of 6-Methylpurine and 2-Fluoroadenine in Human C ells Biochemical Pharmacology, vol. 55, pp. 1673-1681.

Puhlman et al. (1999) Thymidine Kinase-Deleted Vaccina Virus Expressing Purine Nucleoside Phosphorylase as a Vector for Tumor-Directed Gene Therapy Human Gene Therapy, 10:649-657.

Reese (1968) Extracellular Purine β-ribosidases from Fungi Canadian Journal of Microbiology, 14:377-383.

Schmidt and Königk (1975) A Purine Nucleoside Hydrolase from *Trypansoma gambiense*, Purification and Properties Tropenmed. Parasit., 26:19-26.

Secrist et al. (1999) Gene Therapy of Cancer: Activation of Nucleoside Prodrugs with E.coli Purine Nucleoside Phosphorylase Nucleosides Nucleotides 1999 Apr./May; 18 (4-5): 745-57.

Senesi et al. (1976) A Specific Adenosine Phosphorylase, Distinct from Purine Nucleoside Phosphorylase FEBS Letters, vol. 64, No. 2, pp. 353-357.

Shibata et al. (1992) Identification of a *cis*-Acting Element that enhances the Pigment Cell-Specific Expression of the Human Tyrosinase Gene The Journal of Biological Chemistry, vol. 367, No. 29, pp. 20584-20588.

Shirae and Yokozeki (1991) Purifications and Properties of Orotidine-Phosphorolyzing Enzyme and Purine Nucleoside Phosphorylase from *Erwinia carotovora* AJ 2992 Agric. Biol. Chem., 55(7), 1849-1857.

Sorscher and Huang (1991) Diagnosis of Genetic Disease by Primer-Specified Restriction Map Modification with Application to Cystic Fibrosis and *Retinitis pigmentosa* The Lancet, vol. 1115-1118.

Sorscher et al. (1994) Tumor Cell Bystander Killing in Colonic Carcinoma Utilizing the *Escherichia coli* DeoD Gene to Generate Toxic Purines Gene Therapy, 1-233-238.

Springer and Niculescu-Duvaz (2000) Prodrug-Activating Systems in Suicide Gene Therapy The Journal of Clinical Investigation, vol. 105, No. 9, pp. 1161-1167.

Stoeckler et al. (1997) Purine Nucleoside Phosphorylase. 3. Reversal of Purine Base Specificity by Site-Directed Mutagenesis Biochemistry, vol. 36, No. 39, pp. 11749-11756.

Streeter et al. (1980) 7-ribosyl-3-deazaguanine—Mechanism of Antibacterial Action Biochemical Pharmacology, vol. 29, pp. 1791-1797.

Tannock (1989) Principles of Cell Proliferation: Cell Kinetics Devita and Hellman, eds. (L.B. Lippincot, Philadelphia), pp. 3-13, reproduced with permission from: Tannock IF, Hill RP: The Basice Science of Oncology Elmsford NY Pergamon Press, 1987.

Tapscott et al. (1994) Gene Therapy of Rat 9L Gliosarcoma Tumors by Transduction with Selectable Genes Does Not Require Drug Selection Proc. Natl. Acad. Sci. USA, vol. 91, pp. 8185-8189.

Tarr (1958) Lingcod Muscle Purine Nucleoside Phosphorylase Can. J. Biochem. Physiol., 36:517-530.

Tham et al. (1993) Identification of *Mycoplasma pirum* Genes Involved in the Salvage Pathways for Nucleosides Journal of Bacteriology, vol. 175, No. 16, pp. 5281-5285.

Trembacz and Jezewska (1993) Specific Adenosine Phophorylase from Hepatopancreas of Gastropod *Helix pomatia* Comp. Biochem. Physiol., vol. 104B, No. 3, pp. 481-487.

Trinh et al. (1995) Enzyme/Prodrug Gene Therapy: Comparison of Cytosine Deaminanse/5-Fluorocytosine Versus Thymidine Kinase/Ganciclovir Enzyme/Prodrug Systems in a Human Colorectal Carcinoma Cell Line Cancer Research, 55:4808-4812.

Van Berkel et al. (1991) Receptor-Dependent Targeting of Lipoproteins to Specific Cell Types of the Liver Targeted Diagnosis and Therapy, 5:225-219.

Wagner et al. (1990) Transferrin-Polycation Conjugates as Carriers for DNA Uptake into Cells Proc. Natl. Acad. Sci. USA, 87:3410-3414.

White et al. (1982) Comparison of the Actions of 9-β-D-Arabinofuranosyl-2-Fluoroadenine and 9-β-D-Arabinofuranosyladenine on Target Enzymes from Mouse Tumor Cells Cancer Research, 42:2260-2264.

Williams et al. (1984) Human Purine Nucleoside Phosphorylase cDNA Sequence and Genomic Clone Characterization Nucleic Acids Research, vol. 12, No. 14, pp. 5779-5787.

Wu and Wu (1988) Receptor-Mediated Gene Delivery and Expression *in vivo* J. Biol. Chem., 263, 29:14621-14624.

Xu and McLeod (2001) Strategies for Enzyme/Prodrug Cancer Therapy Clinical Cancer Research, vol. 7, pp. 3314-3324.

Fick et al (1995) The Extent of Heterocellular Communication Mediated by Gap Junctions is Predictive of Bystander Tumor Cytotoxicity *In Vitro* Proc. Natl. Acad. Sci. USA, vol. 92, pp. 11071-11075, Nov. 1995, Medical Sciences.

* cited by examiner

MUTANT PURINE NUCLEOSIDE PHOSPHORYLASE PROTEINS AND CELLULAR DELIVERY THEREOF

GRANT REFERENCE

The research carried out in connection with this invention was supported in part by grant #U19-CA67763 from the National Cancer Institute.

BACKGROUND OF THE INVENTION

1. Field of the Invention

This invention relates to mutant purine nucleoside phosphorylase enzymes having different activity than the non-mutant purine nucleoside phosphorylase enzyme, and to substrates for these mutant enzymes. In particular the invention relates to a mutant M65V having greater activity than the wild-type enzyme in cleaving specific substrates.

2. Description of the Related Art

A prodrug activation strategy for selectively impairing tumor cells involves the expression of a gene encoding an exogenous enzyme in the tumor cells and administration of a substrate for that enzyme. The enzyme acts on the substrate to generate a substance toxic to the targeted tumor cells. This technique has advantages over the expression of directly toxic genes, such as ricin, diphtheria toxin, or pseudomonas exotoxin. These advantages include the capability to (1) titrate cell impairment, (2) optimize therapeutic index by adjusting either levels of prodrug or of recombinant enzyme expression, and (3) interrupt toxicity by omitting administration of the prodrug. In addition, this technique uses prodrugs found to have different effects on different cell types, allowing treatment to be adjusted according to a specific disease state.

Enzymes useful in a prodrug activation approach have been described and include enzymes such as thymidine kinase, cytosine deaminase and purine nucleoside phosphorylase, as described in U.S. Pat. Nos. 5,338,678, 5,552,311, 6,017,896 and 6,207,150. However, the effectiveness of tumor treatment using prodrug activation techniques may be limited in cases where side-effects of substrate administration are present. For example, the prodrug ganciclovir, often used in combination with thymidine kinase, can cause unwanted immunosuppressive effects. In the case of purine nucleoside phosphorylase therapy, undesirable side-effects may occur due to the activity of endogenous human and E. coli purine nucleoside phosphorylases present in human cells and in normal intestinal flora respectively.

Thus, there exists a need for a prodrug activation method for treating tumors that overcomes the problem of side effects.

SUMMARY OF THE INVENTION

A nucleotide sequence is provided that encodes a mutant purine cleaving enzyme that has different biological activity than a wild-type purine cleaving enzyme. In particular, mutant E. coli derived purine nucleoside phosphorylase (PNP) and nucleoside hydrolase proteins are provided. More specifically, a nucleotide sequence is described (M65V:SEQ ID NO: 1) that encodes a mutant E. coli derived PNP protein which has valine substituted for a methionine at position 65 (counting from the fmet) (M65V:SEQ ID NO: 2). In addition, a nucleotide sequence is provided (A157V:SEQ ID NO: 3) that encodes a mutant E. coli derived PNP protein which has valine substituted for an alanine at position 157 (A157V:SEQ ID NO: 4), position 157 if counting from the fmet. Further, mutant E. coli derived purine nucleoside phosphorylase (PNP) proteins are provided having different activity in cleaving a purine nucleoside analog substrate compared with a wild-type E. coli derived purine nucleoside phosphorylase.

A recombinant vector containing a nucleotide sequence of the present invention is described. Further detailed are vectors which contain a nucleotide sequence encoding a mutant E. coli derived purine nucleoside phosphorylase protein of the present invention. Also described is a host cell transformed with a vector of the present invention.

A recombinant expression vector is provided which contains the nucleotide sequence of a mutant E. coli derived PNP protein, M65V. Further, recombinant vectors are provided which contain the nucleotide sequence of one of the mutant E. coli derived PNP proteins: A157V, M65V, M65A, M65I, M65Q, H5N, A157F, A157L, E180D, E180N, E180S, E180T, M181A, M181L, M181N, M181V, M181E, E182A, E182Q, E182V, D205A and D205N.

Also provided is a recombinant virus which is capable of carrying a gene to a target cell and which contains the nucleotide sequence of a mutant purine cleaving enzyme of the present invention. Further described is a recombinant virus containing a nucleotide encoding a mutant E. coli derived purine cleaving enzyme such as M65V. Recombinant viruses are provided which are capable of carrying a gene to a target cell and which contain a nucleotide sequence of one of the mutant E. coli derived PNP proteins: A157V, M65V, M65A, M65I, M65Q, H5N, A157F, A157L, E180D, E180N, E180S, E180T, M181A, M181L, M181N, M181V, M181E, E182A, E182Q, E182V, D205A and D205N.

A recombinant mutant purine cleaving enzyme having different biological activity than a wild-type is provided. In particular, recombinant mutant E. coli PNPs are detailed having different biological activity than a wild-type E. coli PNP.

Also described is a process for impairing a cell which includes the steps of administering a nucleotide sequence encoding a mutant purine cleaving enzyme of the present invention to a target cell and delivering an effective amount of a prodrug. More specifically, a process is provided for treatment of abnormal cell growth and pathological viral infection by administering a mutant E. coli PNP to a cell and delivering a suitable PNP substrate in order to produce a toxin and thereby impair the cell. In particular, a process for impairing a cell is described in which a mutant E. coli PNP M65V is administered to a target and an effective amount of a prodrug is delivered. A process for impairing a cell is described in which a mutant E. coli PNP M65V is administered to a target and an effective amount of 9-(6,7-dideoxy-α-L-hept-6-ynofuranosyl)-6-methylpurine is delivered. A process for impairing a cell is described in which a mutant E. coli PNP M65V is administered to a target and an effective amount of 9-(α-L-lyxofuranosyl)-2-fluoro-adenine is delivered. A process for impairing a cell is described in which a mutant E. coli PNP M65V is administered to a target and an effective amount of 9-(6-deoxy-α-L-talofuranosyl)-6-methylpurine is delivered.

Commercials kits are described for impairing a cell which include a vector containing a nucleotide sequence encoding an amino acid sequence depicted as SEQ ID No. 2, a purified mutant PNP as depicted by SEQ ID No. 2 or a recombinant virus containing a nucleotide sequence encoding the mutant PNP depicted by SEQ ID No. 2.

DETAILED DESCRIPTION OF THE INVENTION

The enzymes which are the subject of the present invention are purine cleaving enzymes such as purine nucleoside phosphorylases and nucleoside hydrolases. Methylthioadenosine phosphorylase is illustrative of a subclass of purine nucleoside phosphorylases also the subject of the present invention. Purine nucleoside phosphorylases and nucleoside hydrolases are present in diverse organisms illustratively including mammals such as humans, and microorganisms, such as *Leishmania donovani; Trichomomas vaginalis; Trypanosoma cruzi; Schistosoma mansoni; Leishmania tropica; Crithidia fasciculata; Aspergillis* and *Penicillium; Erwinia carotovora; Helix pomatia; Ophiodon elongatus; Salmonella typhimurium; Bacillus subtilis; Clostridium; mycoplasma; Trypanosoma gambiense; Trypanosoma brucei; Sulfolobus solfataricus; E. coli*.

A nucleoside phosphorylase catalyzes the reaction: purine analog nucleoside+$PO_4$→ribose-1-$PO_4$ (or deoxyribose-1-phosphate)+toxic purine analog. The present invention provides nucleotide sequences and amino acid sequences encoding mutant purine cleaving enzymes having different biological activity in cleaving specific substrates compared to the wild-type enzyme. In a preferred embodiment, the purine nucleoside phosphorylase (PNP) mutants of the present invention are genetically modified bacterial PNPs capable of reacting with a specific substrate or substrates that the native PNPs will not recognize or recognize poorly. However, any mutant purine cleaving enzyme which can selectively convert a substrate to produce a toxic purine analog can be utilized. For example, as described below, a mutant *E. coli* PNP enzyme is designed according to the present invention to act on compounds with substituents on the 5'-carbon that are poor substrates for wild-type enzyme.

The term "biological activity" as used herein is intended to mean a measurement of the amount of end product produced by the reaction of a specified amount of a mutant or wild-type purine cleavage enzyme in the presence of a substrate in a period of time measured by appropriate method as shown in Example 1.

A compound which is a substrate for the enzyme to produce a toxic substance which impairs a cell is referred to herein interchangeably as a "prodrug" or a "substrate."

The term "mutant" as used herein is intended to mean a modified protein which differs from the wild-type protein.

The term "pathogenic viral infection" as used herein is intended to mean infection by a virus causing disease or pathological effects.

The term "pharmaceutically acceptable" as used herein is intended to mean a material that is not biologically or otherwise undesirable, which can be administered to an individual without causing significant undesirable biological effects or interacting in a deleterious manner with any of the other components of the pharmaceutical composition in which it is contained.

Purine Cleavage Enzyme Mutants

Purine cleavage enzyme mutants having different biological activity than wild-type PNP in cleaving selected substrates are generated by omitting, adding, and/or exchanging at least a single amino acid for another amino acid at the same position in the PNP sequence. In a preferred embodiment, the PNP mutants have greater activity than wild-type PNP.

Mutagenesis can be performed utilizing any one of several techniques known to those of skill in the art. For example, a particular mutagenesis protocol is followed utilizing the Quickchange Site-Directed Mutagenesis Kit from Stratagene (La Jolla, Calif.). This procedure requires the use of two complementary synthetic oligonucleotide primers, each encoding the intended nucleotide change, with length and sequence also dictated by the nucleotides flanking the change site according to parameters described in the kit manual. Double-stranded plasmid DNA, comprising the DNA sequence to be mutagenized/changed, serves as the mutagenesis template. The mixed primers are annealed to heat denatured template DNA and extended using free deoxy-nucleotides and the thermostable high-fidelity Pfu DNA polymerase. Multiple rounds of heat denaturation, annealing and extension are performed in a thermocycler to produce adequate quantities of linear single-stranded plasmid representing each complementary strand of the plasmid template. As each de novo strand arises from the extended mutagenesis primer, it also contains the intended nucleotide change. As the complementary strands anneal, the primary product is double-stranded plasmid, circularized by annealing through the overlap provided by the complementary primers. To eliminate the residual template DNA, the product is digested with restriction endonuclease Dpn I which selectively cleaves DNA that has been modified by in vivo methylation at its recognition site; because the in vitro synthesized mutagenesis product is not methylated, it survives the treatment with Dpn I. The newly synthesized, annealed, circularized and Dpn I digested plasmid DNA containing the nucleotide change is used to transform competent *E. coli* cells. Cell colonies arising from this transformation are screened by DNA sequence analysis to verify their containing the mutant sequence.

In a variation of the Quickchange procedure as described in the kit manual, the following changes can be made. The nucleotides, buffers and enzymes used may, or may not, be components of the commercially available kit. The reaction mix is made or 300 nM with each primer. After the recommended number of cycles in the thermocycler, the reaction mix is checked by electrophoresis of a small aliquot through a 0.8–1.0% agarose gel to confirm the existence of de novo plasmid DNA. Following digestion with Dpn I, excess primer is removed by purification of the plasmid DNA using the QIAquick PCR Purification Kit from Qiagen (Valencia, Calif.). The purified DNA is then heated to remove any residual primer from the linear plasmid ends, and then cooled to allow annealing of the complementary ends before transformation of the *E. coli* cells.

Mutagenesis can also be performed as described in Maniatis, et al., *Molecular Cloning: A Laboratory Manual*, $2^{nd}$ Ed. Cold Spring Harbor, N.Y.: CSHL Press. In an example of such a procedure, the wild-type PNP nucleotide sequence is subcloned into a bacteriophage M13 vector and single-stranded DNA is prepared as described by Maniatis. An oligonucleotide primer is designed for each mutation. The oligonucleotide primer has the same sequence as a portion of the wild-type sequence except at the site of the desired mutation where one or two nucleotides are substituted for the wild-type nucleotides. The length of the oligonucleotide primer depends on the exact sequence in the area of the desired mutation and is determined as described in Maniatis. The mutagenic oligonucleotide primer is phosphorylated with T4 polynucleotide kinase by mixing 100–200 pmoles of the mutagenic oligonucleotide with 2 microliters of 10× bacteriophage T4 polynucleotide kinase buffer, 1 microliter of a 10 millimolar solution of ATP, 4 units of bacteriophage T4 polynucleotide kinase and water to a total reaction volume of 16.5 microliters. The 10× bacteriophage T4 polynucleotide kinase buffer is composed of 0.5 M Tris.Cl (pH 7.6), 0.1 M $MgCl_2$, 50 millimolar dithiothreitol, 1 millimolar spermidine HCl and 1 millimolar EDTA. The reaction is incubated for 1 hour at 37° C. and then heated at 68° C. for 10 minutes. The mutagenic oligonucleotide primer is annealed to single-stranded DNA in a mixture of 0.5 pmole single-stranded DNA, 10 pmoles phosphorylated mutagenic oligonucleotide, 10 pmoles non-phosphorylated universal sequencing primer complementary to a region of the vector, 1 microliter of 10× PE1 buffer and water to a total reaction volume of 10 microliters. The 10× PE1 buffer is composed of 200 millimolar Tris base, pH 7.5, 500 millimolar NaCl, 100 millimolar $MgCl_2$ and 10 millimolar dithiothreitol. The mixture is heated to a temperature 20° C. above the theoretical $T_m$ of a perfect hybrid formed between the mutagenic oligonucleotide for 5 minutes. The theoretical $T_m$ is calculated from the formula $Tm=4(G+C)+2(A+T)$. The mixture is allowed to cool to room temperature over a period of about 20 minutes. Primer extension and ligation are performed by mixing 1 microliter of 10× extension buffer (which is composed of 200 millimolar Tris base, pH 7.5, 100 millimolar $MgCl_2$, 100 millimolar dithiothreitol), 1 microliter of 10 millimolar ATP, water to 8.5 microliters, 1 microliter of a solution of the four dNTPs (dGTP, dATP, dTTP, and dCTP), each at a concentration of 2 millimolar, 5 Weiss units of T4 DNA ligase and 2.5 units of Klenow fragment of E. coli DNA polymerase I. Ten microliters of the primer extension/ligation mixture are added to the single-stranded DNA/oligonucleotide mixture. The reaction is then incubated at 16° C. for 6–15 hours.

The reaction mixture is then used to transform E. coli of an appropriate strain and plaques are screened by hybridization with an appropriate labeled probe, e.g. the mutagenic oligonucleotide primer.

Specific mutants generated include: A157V, M65V, M65A, M65I, M65Q, H5N, A157F, A157L, E180D, E180N, E180S, E180T, M181A, M181L, M181N, M181V, M181E, E182A, E182Q, E182V, D205A and D205N. The DNA sequence of mutant M65V (M65V:SEQ ID NO: 1) is provided. The mutation ATG→gtt appears at bp 193. The corresponding amino acid sequence of M65V (M65V:SEQ ID NO: 2) has the position 65 methionine to valine mutation. It will be appreciated by those skilled in the art that, due to the degeneracy of the amino acid code, multiple nucleic acid sequences may encode the same amino acid sequence. For example, valine is encoded by nucleotides gtt and by nucleotides gtc, gta and gtg. The nucleic acid codons encoding any particular amino acid are well known to those skilled in the art.

Table I summarizes the activity of 22 mutants with substrates MeP-dR and F-araA. The results are presented as the percent of wild-type activity. Of the 22 mutants in Table I, M65V, A157L, A157V and E180D retained some appreciable level of activity toward these substrates. Abbreviations used may include: MeP-dR: 9-(2-deoxy-β-D-ribofuranosyl)-6-methylpurine; F-araA: 9-(β-D-arabinofuranosyl)-2-fluoroadenine; 5'-methyl(allo)-MeP-R: 9-(6-deoxy-β-D-allofuranosyl)-6-methylpurine; 5'-methyl(talo)-MeP-R: 9-(6-deoxy-α-L-talofuranosyl)-6-methylpurine; F-Ade: 2-fluoroadenine; 5'-methyl(talo)-2-F-adenosine: 9-(6-deoxy-α-L-talofuranosyl)-2-fluoroadenine.

TABLE I

Summary of mutant E. coli PNP activity with MeP-dR and F-araA

| Mutant | MeP-dR | F-araA |
|---|---|---|
| | Percent of Control Activity | |
| Wild-type | 100 | 100 |
| Not transfected | 0.8 | 3 |
| H5N | 0.08 | 0.15 |
| M65A | 1.5 | 1.6 |
| M65I | 0.02 | 0.15 |
| M65Q | 0.6 | 1.0 |
| M65V | 42 | 37 |
| A157F | 1.5 | 1.4 |
| A157L | 12 | 21 |
| A157V | 118 | 146 |
| E180D | 81 | 60 |
| E180N | 0.2 | 0.3 |
| E180S | 0.5 | 0.8 |
| E180T | 0.06 | 0.1 |
| M181A | 0.04 | 0.2 |
| M181L | 0.6 | 1.6 |
| M181N | 0.1 | 0.4 |
| M181V | 0.02 | 0.07 |
| M181E | 0.04 | 0.1 |
| E182A | 0.5 | 0.9 |
| E182Q | 0.6 | 1.0 |
| E182V | 0.3 | 0.6 |
| D205A | 1.0 | 1.1 |
| D205N | 2.2 | 2.4 |

The key requirement of the mutant PNP nucleotide sequence is that it must encode a functional mutant enzyme that is able to recognize and act upon a specific substrate with different biological activity in producing a cytotoxic compound than the wild-type enzyme. Two E. coli mutants, M65A and M65V, are tested with various purine analog substrates with which the wild-type enzyme has lower activity than with MeP-dR, as shown in Table II.

TABLE II

| Substrate | Wild-type PNP | M65A | M65V |
|---|---|---|---|
| | nmoles/mg/hour (percent of wild-type activity) | | |
| MeP-dR | 628,000 | 9,700 (1.5%) | — |
| | 560,000 | 9,600 (1.7%) | — |
| | 1,400,000 | — | 800,000 (57%) |
| 5'methyl(allo)-MeP-R | 150 | 13 | 320 |
| | 64 | 5 | 163 |
| 5'-methyl(talo)MeP-R | 950 | 910 (96%) | — |
| | 1630 | 1360 (84%) | — |
| | 1278 | — | 33,600 (2600%) |
| | 3200 | 2160 (68%) | >61,000 (1900%) |
| | 2350 | — | 115,000 (4900%) |
| 9-(α-L-lyxofuranosyl)-adenine | 5,133 | 696 (14%) | — |
| | 4,130 | 900 (22%) | — |
| | 11,800 | — | 70,000 (593%) |
| 5'-amino-5'-deoxy-Ado | 623 | 29 (5%) | — |
| | 882 | — | 832 (94%) |

Table II shows the activity of these mutant E. coli PNP enzymes compared to wild-type PNP in the presence of various substrates. Activity of the M65V mutant is 38-fold greater than wild-type PNP using 5'-methyl(talo)MeP-R as a substrate and 6-fold (593%) greater than wild-type PNP using 9-(α-L-lyxofuranosyl)-adenine as a substrate. It is appreciated that the greater biological activity of the mutants will allow for greater activity in impairing abnormal cell growth when these mutant are used for treatment of pathological conditions. In addition, it is appreciated that tumors expressing the M65V E. coli PNP would be at least 80-fold more sensitive to 5'-methyl(talo)MeP-R or 5'-methyl(talo)-2-F-adenosine than tumors expressing wild-type PNP would be to F-araA. It is further appreciated that since the M65V mutant cleaved 5'-methyl(talo)MeP-R 80 times better than the wild-type enzyme cleaved F-araA, and since F-araA caused complete responses in tumor expressing wild-type enzyme, an at least 80-fold increase in the generation of F-Ade using the M65V mutant and 5'-methyl(talo)-2-F-adenosine combination will lead to even better anti-tumor activity.

To further explore mutant activity, M65V mutant was exposed to various nucleoside analog compounds. The activity, as compared to wild-type PNP, is summarized in Table III where parenthetical data is indicative of the number of experiment measurements.

TABLE III

Activity of E. coli PNP mutant M65V with various nucleoside analogs

| Compound | Wild type Pure enzyme | M64V crude extract nmole/mg/hr | M64V pure enzyme |
|---|---|---|---|
| 9-(β-D-ribofuranosyl)-6-fluoromethylpurine | 56,000 (1) | | 211,000 (1) |
| 9-(β-D-ribofuranosyl)-6-methylpurine | 100,000 (4) | | 140,000 (2) |
| 9-(2-deoxy-β-D-ribofuranosyl)-6-methylpurine | 528,000 (16) | 535,000 (6) | 593,000 (4) |
| 9-(2-deoxy-α-D-ribofuranosyl)-6-methylpurine | — (1*) | — (2) | |
| 9-(β-D-arabinofuranosyl)-6-methylpurine | 14 (2) | 3 (2) | |
| 9-(β-D-xylofuranosyl)-6-methylpurine | — (1*) | — (2) | |
| 7-(β-D-ribofuranosyl)-6-methylpurine | — (2) | — (2) | |
| 9-(α-L-lyxofuranosyl)-6-methylpurine | 218 (3) | | 9,600 (3) |
| 7-(α-L-lyxofuranosyl)-6-methylpurine | — (1) | | — (1) |
| 9-(6-deoxy-β-D-allofuranosyl)-6-methylpurine | 47 (3) | 316 (4) | |
| 9-(6-deoxy-α-L-talofuranosyl)-6-methylpurine | 915 (3) | 75,000 (7) | 76,000 (2) |
| 9-(5-deoxy-5-phenylthio-β-D-ribofuranosyl)-6-methylpurine | — (2) | — (1) | |
| 9-(6,7-dideoxy-β-L-talo/β-D-allo-hept-6-ynofuranosyl)-6-methylpurine | — (1) | 119 (3) | |
| 9-(5-deoxy-5-iodo-β-D-ribofuranosyl)-6-methylpurine | — (1) | | — (1) |
| 9-(5,5-di-C-methyl-β-D-ribofuranosyl)-6-methylpurine | — (1) | | 230 (1) |
| 9-(β-D-arabinofuranosyl)-2-fluoroadenine | 1,250 (6) | 904 (3) | |
| 9-(5-deoxy-5-methylthio-β-D-ribofuranosyl)-2-fluoroadenine | 13 (1) | | 2500 (1) |
| 9-(5-deoxy-5-iodo-β-D-ribofuranosyl-2-fluoroadenine | 13 (1) | | 490 (1) |
| 9-(α-L-lyxofuranosyl)-adenine | 3,690 (6) | 54,000 (4) | |
| 9-(β-D-lyxofuranosyl)-adenine | — (1) | — (2) | |
| 9-(β-D-allopyranosyl)-adenine | — (2) | — (2) | |
| 9-(β-D-fructopyranosyl)-adenine | — (2) | — (2) | |
| 9-(β-D-ribopyranosyl)-adenine | — (2) | — (2) | |
| adenosine 5'-carboxamide | — (1) | — (2) | |
| 5'-amino-5'-deoxyadenosine | 539 (1) | 930 (4) | |
| 3'-deoxyadenosine | — (2) | — (2) | |
| 9-(α-D-arabinofuranosyl)-adenine | — (1*) | — (2) | |
| 2'-O-methyl-adenosine | — (2) | — (2) | |
| 5'-deoxy-5'-methylthio-adenosine | — (2) | | 690 (1) |
| 9-(2-deoxy-β-L-ribofuranosyl)-2-chloroadenine | — (1*) | — (2) | |
| 9-(2-deoxy-α-L-ribofuranosyl)-2-chloroadenine | — (1*) | — (2) | |
| guanosine | 242 (2) | — (2) | 778,000 (1) |
| 9-(2,3-dideoxy-3-hydroxymethyl-α-D-ribofuranosyl)-6-thioguanine | | | |

Enzymes were mixed with 100 μM of each substrate shown in the table and the rate of cleavage was determined by HPLC separation of base from nucleoside. The numbers in parenthesis are the number of separate experiments that were averaged to obtain the value shown.

—No detectable activity at 100 μg/ml (limit of detection approximately 1 nmole/mg/hr).

*Result confirmed with crude E. coli PNP preparation.

Table IV shows the activity of five E. coli PNP mutant enzymes compared with wild-type (WT) PNP in the presence of various substrates.

the activity of wild-type PNP using MeP-dR as a substrate and approximately 150% of the activity of wild-type PNP using F-araA as a substrate.

TABLE IV

|  | MeP-dR | allo-met | talo-met | 5'-NH$_2$ | allo-acet | talo-acet | α-L-lyxo | 5'CONH$_2$ | 5'-S-phenyl |
|---|---|---|---|---|---|---|---|---|---|
| WT | — | 150 | — | 960 | — | — | — | — | — |
|  | 740,000 | 64 | 962 | 1270 | 0 | 0 | 4500 | 18 | — |
|  | — | — | — | — | — | — | — | — | 0 |
| M65V | 524,000 | 320 | 92,000 | 760 | 0 | 190 | 58,000 | 22 | — |
|  | 281,000 | 163 | 44,700 | 1150 | 0 | 78 | 27,300 | 4 | — |
|  | — | — | — | — | — | — | — | — | 0 |
| M65A | 12,000 | 13 | 2,400 | 42 | 0 | 240 | 1,500 | 23 | — |
|  | 9,400 | 5 | 1160 | 0 | 0 | 66 | 1,070 | 3 | — |
| M65I | 260 | 2 | 30 | 0 | 0 | 0 | 118 | 25 | — |
|  | 127 | 0 | 11 | 67 | 0 | 0 | 34 | 7 | — |
| M65Q | 6050 | 12 | 120 | 26 | 0 | 0 | 239 | 10 | — |
|  | 4210 | 0 | 59 | 42 | 0 | 0 | 112 | 4 | — |
| H5N | 570 | 0 | 4 | 12 | 0 | 0 | 16 | 23 | — |
|  | 280 | 3 | 0 | 59 | 0 | 0 | 11 | 4 | — |

Abbreviations - allo-met: 9-(6-deoxy-β-D-allofuranosyl)-6-methylpurine; talo-met: 9-(6-deoxy-α-L-talofuranosyl)-6-methylpurine; 5'-NH2: 5'-amino-5'-deoxyadenosine; allo-acet: 9-(6,7-dideoxy-β-D-hept-6-ynofuranosyl)-6-methylpurine; talo-acet: 9-(6,7-dideoxy-α-L-hept-6-ynofuranosyl)-6-methylpurine; α-L-lyxo: 9-(α-L-lyxofuranosyl)-adenine; 5'-CONH2: adenosine5'-carboxamide; 5'-S-phenyl: 9-(5-deoxy-5-phenylthio-β-D-ribofuranosyl)-6-methylpurine; MeP-dR: 9-(2-deoxy-β-D-ribofuranosyl)-6-methylpurine; F-araA: 9-(β-D-arabinofuranosyl)-2-fluoroadenine; 5'-methyl(allo)-MeP-R: 9-(6-deoxy-β-D-allofuranosyl)-6-methylpurine; 5'-methy(talo)-MeP-R: 9-(6-deoxy-α-L-talofuranosyl)-6-methylpurine; F-Ade: 2-fluoroadenine; 5'-methyl(talo)-2-F-adenosine: 9-(6-deoxy-α-L-talofuranosyl)-2-fluoroadenine.
Activity values are given in nmoles/mg/hour. "—" denotes no measurement was made; while "0" denotes no measurable activity.

The kinetic constants for E. coli PNP mutant M65V with three of the substrates of Table IV are provided herein. This kinetic data is exemplary of the precise activity of substrate compounds with the mutants of the present invention. Table V provides kinetic constants for M65V in comparison to those for wild-type PNP.

TABLE V

Km/Vmax determinations with wild-type and M65V E. coli PNP

| Substrate | $K_m$ (μM) | $V_{max}$ (nmoles/mg/hr) | $r_{coef}$ | $V_{max}/K_m$ | $K_{cat}$ (min$^{-1}$) |
|---|---|---|---|---|---|
| Wild-type enzyme |  |  |  |  |  |
| MeP-dR | 140 | 1,810,000 | 0.999 | 12,900 | 723 |
|  | 111 | 1,100,000 | 0.988 | 9,900 | 440 |
| 5'-methyl(talo)-MeP-R | 2,980 | 9,116 | 0.999 | 3 | 4 |
|  | 3,000 | 31,700 | 0.999 | 11 | 13 |
| 9-(α-L-lyxofuranosyl)- adenine | 1,370 | 19,200 | 0.998 | 14 | 8 |
|  | 1,340 | 57,700 | 0.978 | 43 | 23 |
| M65V |  |  |  |  |  |
| MeP-dR | 359 | 2,550,000 | 0.997 | 7100 | 1020 |
|  | 313 | 2,409,000 | 0.998 | 7700 | 963 |
| 5'-methyl(talo)-MeP-R | 216 | 212,000 | 0.997 | 981 | 85 |
|  | 248 | 252,000 | 0.998 | 1016 | 101 |
|  | 292 | 255,000 | 0.994 | 873 | 102 |
| 9-(α-Iyxofuranosyl)- adenine | 196 | 215,000 | 0.999 | 1100 | 86 |
|  | 203 | 162,000 | 0.989 | 798 | 65 |
|  | 237 | 174,000 | 0.975 | 734 | 70 |

In yet another preferred embodiment, the PNP used in the present methods includes a modified PNP having different biological activity than wild-type PNP in cleaving substrates MeP-dR and F-araA. Mutant A157V, has a substitution of the alanine at position 158, counting the fmet as position 1, by a valine. Mutant A157V PNP has approximately 120% of A method is presented below by which any mutant PNP or other purine analog nucleoside cleavage enzyme can be tested in a cell for its ability to convert a given substrate from a relatively nontoxic form to a cytotoxic product.

Substrate Selection

Suitable substrates are characterized by being relatively non-toxic to a mammalian cell compared to the toxic cleaved purine base analog. Below are listed some illustrative examples of substrates. Common abbreviations are included after some of the compounds.

9-(2-deoxy-β-D-ribofuranosyl]-6-methylpurine; MeP-dR
9-(β-D-ribofuranosyl)-2-amino-6-chloro-1-deazapurine; ACDP-R
7-(β-D-ribofuranosyl)-3-deazaguanine
9-(β-D-arabinofuranosyl)-2-fluoroadenine; F-araA, Fludarabine
2-fluoro-2'-deoxyadenosine; F-dAdo
9-(5-deoxy-β-D-ribofuranosyl)-6-methylpurine
2-fluoro-5'-deoxyadenosine
2-chloro-2'-deoxyadenosine; Cl-dAdo, Cladribine
5'-amino-5'-deoxy-2-fluoroadenosine
9-(5-amino-5-deoxy-β-D-ribofuranosyl)-6-methylpurine
9-(α-D-ribofuranosyl)-2-fluoroadenine
9-(2,3-dideoxy-β-D-ribofuranosyl)-6-methylpurine
2',3'-dideoxy-2-fluoroadenosine
9-(3-deoxy-β-D-ribofuranosyl]-6-methylpurine
2-fluoro-3'-deoxyadenosine In a preferred embodiment, substrates for M65 illustratively include:
9-(α-L-lyxofuranosyl)-2-fluoroadenine
9-(α-L-lyxofuranosyl)-6-methylpurine
9-(6-deoxy-β-D-allofuranosyl)-6-methylpurine
9-(6-deoxy-β-D-allofuranosyl)-2-fluoroadenine
9-(6-deoxy-α-L-talofuranosyl)-6-methylpurine 9-(6-deoxy-α-L-talofuranosyl)-2-fluoroadenine
9-(2,6-dideoxy-β-D-allofuranosyl)-6-methylpurine
9-(2,6-dideoxy-β-D-allofuranosyl)-2-fluoroadenine
9-(2,6-dideoxy-α-L-talofuranosyl)-6-methylpurine
9-(2,6-dideoxy-α-L-talofuranosyl)-2-fluoroadenine
9-(6,7-dideoxy-α-L-hept-6-ynofuranosyl)-6-methylpurine
9-(6,7-dideoxy-α-L-hept-6-ynofuranosyl)-2-fluoroadenine
9-(6,7-dideoxy-β-D-hept-6-ynofuranosyl)-6-methylpurine
9-(6,7-dideoxy-β-D-hept-6-ynofuranosyl)-2-fluoroadenine
9-(2,6,7-trideoxy-α-L-hept-6-ynofuranosyl)-6-methylpurine
9-(2,6,7-trideoxy-α-L-hept-6-ynofuranosyl)-2-fluoroadenine
9-(2,6,7-trideoxy-β-D-hept-6-ynofuranosyl)-6-methylpurine
9-(2,6,7-trideoxy-β-D-hept-6-ynofuranosyl)-2-fluoroadenine
9-(2,3-dideoxy-3-hydroxymethyl-α-D-ribofuranosyl)-6-thioguanine
9-(5,5-di-C-methyl-β-D-ribofuranosyl)-2-fluoro-adenine
9-(5,5-di-C-methyl-β-D-ribofuranosyl)-6-methylpurine
9-(5-deoxy-5-iodo-β-D-ribofuranosyl)-2-fluoroadenine
9-(5-deoxy-5-iodo-β-D-ribofuranosyl)-6-methylpurine
9-(5-deoxy-5-methylthio-β-D-ribofuranosyl)-2-fluoroadenine
9-(5-deoxy-5-methylthio-β-D-ribofuranosyl)-6-methylpurine Further examples are found in Ichikawa E. and Kato K., Curr Med Chem 2001 March; 8(4):385–423. In addition, using ribose- or deoxyribose-containing substrates, *E. coli* PNP can selectively produce a variety of toxic guanine analogs, such as 6-thioguanine or 3-deazaguanine, that are attached to ribose or deoxyribose via the N-7 position in the guanine ring.

Purine analog nucleosides can be tested for activity with individual mutants according to the protocols set forth in Example 1. In a still more preferred embodiment, a substrate for mutant M65V is 9-(α-L-lyxofuranosyl)-2-fluoroadenine, 5'-methyl(talo)-MeP-R or a combination thereof.

It is appreciated that some substrates would be expected to be better tolerated than others. For example, 5'-methyl (talo)MeP-R is preferred in some cases over F-araA since it is over 40-fold less toxic to human cells in culture than F-araA. 5'-methyl(talo)MeP-R is well-tolerated when given at 200 mg/kg body weight once a day for three consecutive days in mice.

Vectors Containing Mutant PNP Encoding Nucleic Acids

The present invention provides a vector containing a DNA sequence encoding a mutant *E. coli* purine nucleoside phosphorylase protein. The vector may further contain a regulatory element operably linked to the nucleotide sequence such that the nucleotide sequence is transcribed and translated in a host. Preferably, the vector is a virus or a plasmid. Illustrative examples of suitable viral vectors include a retrovirus, an adenovirus, an adeno-associated virus, a vaccinia virus, a herpes virus and a chimeric viral construction such as an adeno-retroviral vector. Among useful adenovirus vectors are human adenoviruses such as type 2 or 5 and adenoviruses of animal origin illustratively including those of avian, bovine, canine, murine, ovine, porcine or simian origin.

The use of vectors derived from adeno-associated virus for the transfer of genes in vitro and in vivo has been extensively described, for example in U.S. Pat. No. 4,797,368 and U.S. Pat. No. 5,139,941. In general, the rep and/or cap genes are deleted and replaced by the gene to be transferred. Recombinant viral particles are prepared by cotransfection of two plasmids into a cell line infected with a human helper virus. The plasmids transfected include a first plasmid containing a nucleic acid sequence encoding a mutant PNP of the present invention which is flanked by two inverted repeat regions of the virus, and a second plasmid carrying the encapsidation genes (rep and cap) of the virus. The recombinant viral particles are then purified by standard techniques.

Also provided is a host cell transformed with a vector of the present invention.

Mutant PNP Expression

The mutant PNP enzymes of the present invention are transcribed and translated in vivo and in vitro. In order to produce the proteins in vivo, a vector containing nucleic acids encoding a specific mutant PNP is introduced into cells, in vivo or ex vivo followed by re-introduction of cells back into the animal, via a vector as outlined herein. In another embodiment, the protein of interest is produced in vitro, either in a cell or in a cell-free system. Protein produced in this manner is used in vitro or introduced into a cell or animal to produce a desired result.

Expression of a mutant PNP in mammalian cells may require a eukaryotic transcriptional regulatory sequence linked to the mutant PNP-encoding sequences. The mutant PNP gene can be expressed under the control of strong constitutive promoter/enhancer elements that are contained within commercial plasmids (for example, the SV40 early promoter/enhancer (pSVK30 Pharmacia, Piscataway, N.J., cat. no. 27-4511-01), moloney murine sarcoma virus long terminal repeat (pBPV, Pharmacia, cat. no. 4724390-01), mouse mammary tumor virus long terminal repeat (pMSG, Pharmacia, cat. no. 27-4506-01), and the cytomegalovirus early promoter/enhancer (pCMVβ, Clontech, Palo Alto, Calif., cat. no. 6177-1)).

Selected populations of cells can also be targeted for destruction by using genetic transcription regulatory sequences that restrict expression of the mutant PNP coding sequence to certain cell types, a strategy that is referred to as "transcription targeting." A candidate regulatory sequence for transcription targeting must fulfill two important criteria as established by experimentation: (i) the regulatory sequence must direct enough gene expression to result in the production of enzyme in therapeutic amounts in targeted cells, and (ii) the regulatory sequence must not direct the production of sufficient amounts of enzyme in non-targeted cells to impair the therapeutic approach. In this form of targeting, the regulatory sequences are functionally linked with the PNP sequences to produce a gene that will only be activated in those cells that express the gene from which the regulatory sequences were derived. Regulatory sequences that have been shown to fulfill the criteria for transcription targeting in gene therapy illustratively include regulatory sequences from the secretory leucoprotease inhibitor, surfactant protein A, and α-fetoprotein genes. A variation on this strategy is to utilize regulatory sequences that confer "inducibility" so that local administration of the inducer leads to local gene expression. As one example of this strategy, radiation-induced sequences have been described and advocated for gene therapy applications. It is expected that mutant PNP gene expression could be targeted to specific sites by other inducible regulatory elements.

It may be necessary to utilize tissue-specific enhancer/promoters as a means of directing mutant PNP expression, and thereby PNP-mediated toxicity, to specific tissues. For example, human tyrosinase genetic regulatory sequences are sufficient to direct PNP toxicity to malignant melanoma cells. Mouse tyrosinase sequences from the 5' flanking region (−769 bp from the transcriptional start site) of the gene were capable of directing reporter gene expression to malignant melanoma cells. Although the mouse and human tyrosinase sequences in the 5' flanking region are similar, Shibata et al., *Journal of Biological Chemistry*, 267:20584–20588 (1992) have shown that the human 5' flanking sequences in the same region used by Vile and Hart (−616 bp from the transcriptional start site) did not confer tissue specific expression. Although Shibata et al. suggested that the 5' flanking region would not be useful to target gene expression to tyrosinase expressing cells such as melanomas or melanocytes, a slightly different upstream fragment from that used by Shibata et al., can in fact direct reporter or bacterial PNP gene expression specifically to melanoma cells.

Other tissue-specific genetic regulatory sequences and elements can be used to direct expression of a gene encoding a suitable purine analog nucleoside cleavage enzyme to specific cell types other than melanomas. For example, tissue-specific promoters illustratively including a promoter of albumin, intestinal fatty acid binding protein, milk whey, neurofilament, pyruvate kinase, smooth muscle alpha-actin and villin.

Delivery of a Mutant PNP Gene

A mutant PNP gene of the present invention is delivered in any of a number of forms illustratively including: DNA in the absence of any carriers or stabilizers ("naked DNA"), DNA in the presence of pharmacologic stabilizers or carriers ("formulated DNA"), DNA complexed to proteins that facilitate entry into the cell ("Molecular conjugates"), and DNA complexed to lipids.

The method of delivery of the mutant PNP gene depends on its form and a suitable method will be apparent to one skilled in the art. Such methods illustratively include administration by injection, biolistic transformation and lipofection. The use of lipid-mediated delivery of the mutant PNP gene to mammalian cells is exemplified below. More particularly, cationic liposome-mediated transfer of a plasmid containing a non-human PNP gene is demonstrated. However, other gene transfer methods will also generally be applicable because the particular method for transferring the PNP gene to a cell is not solely determinative of successful tumor cell impairment. Thus, gene transduction, utilizing a virus-derived transfer vector, further described below, can also be used. Such methods are well known and readily adaptable for use in the gene-mediated toxin therapies described herein. Further, these methods can be used to target certain diseases and cell populations by using the targeting characteristics of a particular carrier of the gene encoding a suitable purine analog nucleoside cleavage enzyme such as *E. coli* PNP.

Apathogenic anaerobic bacteria have been used to selectively deliver foreign genes into tumor cells. For example, *Clostridium acetobutylicum* spores injected intravenously into mice bearing tumors, germinated only in the necrotic areas of tumors that had low oxygen tension. Using the assay for PNP activity described below, *Clostridium perfringens* was found to exhibit enzyme activity capable of converting MeP-dR to MeP. This finding suggests a mechanism to selectively express mutant PNP activity in tumor masses with necrotic, anaerobic centers. Thus, tumors can be infected with strains of *Clostridium* expressing mutant PNP and then exposed to an appropriate substrate, such as 9-(α-L-lyxofuranosyl)-2-fluoroadenine, 5'-methyl(talo)-MeP-R or a combination of these. The mutant PNP activity of the clostridium bacteria growing in the anaerobic center of a tumor tissue should then convert the substrate to a toxic nucleoside analog, which then is released locally to impair the tumor cells. Additionally, other bacteria including *E. coli* and *Salmonella* can be used to deliver a mutant PNP or hydrolase gene into tumors.

The rapidly advancing field of therapeutic DNA delivery and DNA targeting also includes vehicles such as "stealth" and other antibody-conjugated liposomes (including lipid-mediated drug targeting to colonic carcinoma), receptor-mediated targeting of DNA through cell specific ligands, lymphocyte-directed tumor targeting, and highly specific therapeutic retroviral targeting of murine glioma cells in vivo (S. K. Huang et al., *Cancer Research*, 52:6774–6781 (1992); R. J. Debs et al., *Am. Rev. Respir. Dis.*, 135:731–737 (1987); K. Maruyama et al., *Proc. Natl. Acad. Sci. USA*, 87:5744–5748 (1990); P. Pinnaduwage and L. Huang, *Biochemistry*, 31:2850–2855 (1992); A. Gabizon and Papahadjopoulas, *Proc. Natl. Acad. Sci. USA*, 85:6949–6953 (1988); S. Rosenberg et al., *New England J. Med.*, 323:570–578 (1990); K. Culver et al., *Proc. Natl. Acad. Sci. USA*, 88:3155–3159 (1991); G. Y. Wu and C. H. Wu, *J. Biol. Chem.*, 263, No. 29:14621–14624 (1988); Wagner et al., *Proc. Natl. Acad. Sci. USA*, 87:3410–3414 (1990); Curiel et al., *Human Gene Ther.*, 3:147–154 (1992); Litzinger, *Biochimica et Biophysica Acta*, 1104:179–187 (1992); Trubetskoy et al., *Biochemica et Biophysica Acta*, 1131:311–313 (1992)). The present approach, within the context of a gene targeting mechanism either directed toward dividing tumor cells or tumor neovascularization, offers an improved means by which a small subset of tumor cells could be established within a growing tumor mass, which would mediate rapid tumor involution and necrosis after the appropriate signal, i.e., after administration of the substrate (prodrug) for a suitable purine analog nucleoside cleavage enzyme, such as a mutant *E. coli* PNP present in or adsorbed to tumor cells.

Methods of Treatment Using a Mutant PNP Enzyme

The method of treatment basically consists of providing the mutant PNP gene to cells and then exposing the cells expressing the mutant PNP gene or protein to an appropriate substrate. The substrate is converted to a toxic substance which impairs the cells expressing the PNP gene. In addition, some cells not expressing the mutant PNP gene are exposed to the toxin and impaired. The observation that non-transfected cells are also impaired has been termed the "bystander effect" or "metabolic cooperation." While not wishing to be limited by theory, it is thought that the toxin produced by interaction of a mutant PNP with a substrate may pass from one cell to another via nucleoside transporters.

A mutant PNP gene can be administered directly to the targeted cells or systemically in combination with a targeting means, such as through the selection of a particular viral vector, delivery formulation or other method as described above. Cells can be treated ex vivo, within the patient to be treated, or treated in vitro, then injected into the patient. Following introduction of the PNP gene into cells in the patient, the prodrug is administered, systemically or locally, in an effective amount to be converted by the mutant PNP into a sufficient amount of toxic substance to impair the targeted cells.

In addition, variable dosing regimens can be used in the method of treatment. A single dose treatment is effective in producing anti-tumor effects as seen in the wild-type. Longer courses of treatment, e.g. several days to weeks, have been used in prodrug therapy with HSV-tk or CD (Ram et al., *Cancer Res.*, 53:83–88 (1993); Dilber et al., *Cancer Res.*, 57:1523–8 (1997); Sacco et al., *Gene Ther.*, 3:1151–1156 (1996); Beck et al., *Human Gene Ther.*, 6:1525–30 (1995); Elshami et al., *Gene Ther.*, 3:85–92 (1996); Fick et al., *Proc. Nat. Acad. Sci. USA*, 92:11071–5 (1995); Imaizumi et al., *Am. J. Resp. Cell & Mole. Biol.*, 18:205–12 (1998); Freeman et al., *Cancer Res.*, 53-5274–83 (1993) and Huber et al., *Proc. Natl. Acad. Sci. USA*, 91:8302–8306 (1994)). The disadvantage of such long-term treatment is evident where there is an endogenous enzyme capable of prodrug conversion to toxin such that cells not targeted by the therapy are affected by the toxin. Thus, the inventive mutant enzymes provide a more effective method with fewer side effects compared to other prodrug/enzyme treatments.

Treatment of Pathological Conditions

A mutant enzyme of the present invention is used to treat a pathological condition by inhibition of targeted cells. Pathological conditions for which such treatment is efficacious illustratively include those characterized by abnormal cell growth such as that occurring in cancer of the bladder, breast, bone, colon, head or neck, kidney, larynx, liver, lung, nasopharynx, oesophagus, ovary, pancreas, prostate, rectum, skin, stomach, thyroid, testicle and uterus as well as other conditions characterized by abnormal cell growth such as myeloid leukaemia, B lymphoma, and glioblastoma.

A mutant *E. coli* PNP gene is used as part of a strategy to treat metastatic solid tumors, such as melanoma, pancreatic, liver or colonic carcinoma. No effective therapy for metastatic tumors of these types currently exists. In this method, a vector containing a mutant PNP gene under the control of a tumor specific promoter is used. For example, the tyrosinase promoter is highly specific for mediating expression in melanoma cells, and will not lead to transgene expression in most tissue types. The mutant PNP gene under the regulatory control of this promoter, therefore, should be activated predominantly within a melanoma tumor and not elsewhere within a patient. Promoters specific for other tumor types, for example, promoters active in the rapidly dividing endothelial cells present in all solid tumors can be used to specifically activate mutant PNP specifically within a primary or metastatic tumor. In a preferred method, a vector containing mutant PNP under the control of a tumor specific promoter is delivered to cells using cationic liposomes. For example, based on animal studies, 100–400 mg plasmid DNA complexed to 1200–3600 micromoles of a 1:1 mixture of the lipids DOTMA (1,2-dioleyloxypropyhl-3-trimethyl ammonium bromide) and DOPE (dioleoyl phosphatidylethanolamine) could be used to deliver the mutant PNP gene to tumor metastases in patients.

A mutant PNP gene can be used to activate prodrugs in the treatment of cancer in the central nervous system. In this method, a cell line producing retroviral particles, in which the viral particles contain the mutant *E. coli* PNP gene, is injected into a central nervous system tumor within a patient. An MRI scanner is used to appropriately inject the retroviral producer cell line to within the tumor mass. Alternatively, the isolated retrovirus particles are injected. Because the retrovirus is fully active only within dividing cells and most of the dividing cells within the cranium of a cancer patient are within the tumor, the retrovirus is primarily active in the tumor itself, rather than in non-malignant cells within the brain. Clinical features of the patient including tumor size and localization, determine the amount of producer cells to be injected. For example, a volume of producer cells in the range of 30 injections of 100 microliters each (total volume 3 ml with approximately $1 \times 10^8$ producer cells/ml injected) are given under stereotactic guidance for surgically inaccessible tumors. For tumors which can be approached intraoperatively, 100 μl aliquots are again injected (at about $1 \times 10^8$ cells/ml) with total injected volumes up to 10 ml using a mutant *E. coli* PNP gene transfer, followed by appropriate substrate administration. This strategy is designed to permit both bystander impairment and toxicity to non-dividing cells.

The destruction of selected populations of cells can be achieved by targeting the delivery of the mutant PNP gene. A vector may contain at least a portion of a virus, bacteria, mammalian cell, non-mammalian cell, DNA molecule, or modified DNA molecule to aid delivery to target cells. The natural tropism or physiology of viral vectors can also be exploited as a means of targeting specific cell types. For example, retroviruses are well known to become fully active only in replicating cells. This fact has been used as the basis for selective retroviral-mediated gene transfer to both human and animal replicating cancer cells growing within a site where normal cells are non-replicating. Alternatively, the viral vector can be directly administered to a specific site such as a solid tumor, where the vast majority of the gene transfer will occur relative to the surrounding tissues. This concept of selective delivery has been demonstrated in the delivery of genes to tumors in mice by adenovirus or herpes virus vectors. Molecular conjugates can be developed so that the receptor binding ligand will bind only to selective cell types, as has been demonstrated for the lectin-mediated targeting of lung cancer.

Recently, it was shown that intravenous injection of liposomes carrying DNA can mediate targeted expression of genes in certain cell types. Targeting of a gene encoding a purine analog nucleoside cleavage enzyme or expression of the gene to a small fraction of the cells in a tumor mass followed by substrate administration could be adequate to mediate involution. Through the increased production of toxin by the mutant enzyme, the present method can be used to destroy the tumor.

Treatment of Virally Infected Cells

In addition to impairing tumor cells, the methods described herein can also be used to virally infected cells. In this embodiment, the selected gene transfer method is chosen for its ability to target the expression of the cleavage enzyme in virally infected cells. For example, virally infected cells may utilize special viral gene sequences to regulate and permit gene expression, that is, virus specific promoters. Such sequences are not present in uninfected cells. If the mutant PNP gene is oriented appropriately with regard to such a viral promoter, the cleavage enzyme would only be expressed within virally infected cells, and not other, uninfected, cells. In another embodiment, the mutant PNP gene is delivered to cells in a vector activated by trans-acting factors present only in virus-infected cells. In these cases, virally infected cells would be much more susceptible to the administration of a substrate designed to be converted to toxic form by a mutant purine nucleoside cleavage enzyme.

Thus, a target in a process for impairing a cell according to the present invention includes a cell, a tissue, an organ, a tumor, a virus, a bacterium, a protozoan and combinations thereof.

Administration of Genetically Engineered Cells

For certain applications, cells that receive the mutant PNP gene are selected and administered to a patient. This method most commonly involves ex vivo co-transfer of both the gene encoding the cleavage enzyme, such as the mutant PNP gene, and a second gene encoding a therapeutic protein gene. The cells that receive both genes are reinfused into the host patient where they can produce the therapeutic protein until the prodrug, such as 9-(α-L-lyxofuranosyl)-2-fluoro-adenine, 5'-methyl(talo)-MeP-R, is administered to eliminate the engineered cells. This method should be useful in "cell therapies," such as those used on non-replicating myoblasts engineered for the production of tyrosine hydroxylase within the brain (Jiao et al., Nature, 362:450 (1993)).

Direct Delivery of the PNP Enzyme to Cells

The bystander impairment conferred by the mutant PNP protein plus prodrug combination can also be achieved by delivering the mutant PNP protein to the target cells, rather than the mutant PNP gene. For example, a mutant PNP enzyme capable of cleaving purine analog nucleosides as described above, is produced ex vivo by available recombinant protein techniques using commercially available reagents. As one example of a method for producing the mutant PNP protein, a mutant E. coli PNP coding sequence is ligated into the multiple cloning site of pGEX-4T-1 (Pharmacia, Piscataway N.J.) so as to be "in frame," with the glutathione-s-transferase (GST) fusion protein using standard techniques. The resulting plasmid contains the GST-PNP fusion coding sequence under transcriptional control of the IPTG-inducible prokaryotic tac promoter. E. coli cells are transformed with the recombinant plasmid and the tac promoter induced with IPTG. IPTG-induced cells are lysed, and the GST-PNP fusion protein purified by affinity chromatography on a glutathione Sepharose 4B column. The GST-PNP fusion protein is eluted, and the GST portion of the molecule removed by thrombin cleavage. All of these techniques and reagents are provided in commercially available kits, for example, one available commercially from Pharmacia, Piscataway, N.J., catalog no. 27-457001. Other methods for recombinant protein production are described in detail in published laboratory manuals.

Since the mutant PNP activates the prodrugs into diffusible toxins, it is only necessary to deliver the mutant PNP protein to the exterior of the target cells prior to prodrug administration. The mutant PNP protein can be delivered to targets by a wide variety of techniques. One example would be the direct application of the mutant protein with or without a carrier to a target tissue by direct application, as might be done by directly injecting a tumor mass within an accessible site. Another example would be the attachment of the mutant PNP protein to a monoclonal antibody that recognizes an antigen on the tumor site. Methods for attaching functional proteins to monoclonal antibodies have been previously described. The mutant PNP conjugated monoclonal antibody is systemically administered, for example, intravenously (IV), and attaches specifically to the target tissue. Subsequent systemic administration of the prodrug will result in the local production of diffusible toxin in the vicinity of the tumor site. A number of studies have demonstrated the use of this technology to target specific proteins to tumor tissue. Other ligands, in addition to monoclonal antibodies, can be selected for their specificity for a target cell and tested according to the methods taught herein.

Another example of protein delivery to specific targets is that achieved with liposomes. Methods for producing liposomes are described e.g., Liposomes: A Practical Approach). Liposomes can be targeted to specific sites by the inclusion of specific ligands or antibodies in their exterior surface, in which specific liver cell populations were targeted by the inclusion of asialofetuin in the liposomal surface (Van Berkel et al., Targeted Diagnosis and Therapy, 5:225–249 (1991)). Specific liposomal formulations can also achieve targeted delivery, as best exemplified by the so-called Stealth™ liposomes that preferentially deliver drugs to implanted tumors (Allen, Liposomes in the Therapy of Infectious Diseases and Cancer, 405–415 (1989)). After the liposomes have been injected or implanted, unbound liposome is allowed to be cleared from the blood, and the patient is treated with the purine analog nucleoside prodrug, such as 9-(α-L-lyxofuranosyl)-2-fluoroadenine or 5'-methyl(talo)-MeP-R, which is cleaved by a mutant E. coli PNP or other suitable cleavage enzyme at the targeted site. Again, this procedure requires only the availability of an appropriate targeting vehicle. In a broader sense, the strategy of targeting can be extended to specific delivery of the prodrug following either mutant PNP protein, or gene delivery.

Administration of Substrates

The formula of Freireich et al., Cancer Chemother. Rep., 50:219–244, (1966) can be used to determine the maximum tolerated dose of substrate for a human subject. For example, based on systemically administered dose response data in mice showing that a dose of 200 mg per kg per day of 5'-methyl(talo)MeP-R for 3 days (3 doses total) was well tolerated, a human dosage of 600 mg 5'-methyl(talo)MeP-R/m$^2$ was determined according to the formula: 200 mg/kg× 3=600 mg/m$^2$. This amount or slightly less should be tolerated in humans with minimal side effects. Furthermore, it is understood that modes of administration that permit the substrate to remain localized at or near the site of the tumor will be effective at lower doses than systemically administered substrates.

The substrate is administered by a route determined to be appropriate for a particular subject by one skilled in the art. For example, the substrate is administered orally, parenterally (for example, intravenously), by intramuscular injection, by intraperitoneal injection, intratumorally, or transdermally. The exact amount of substrate required will vary from subject to subject, depending on the age, weight and general condition of the subject, the severity of the disease that is being treated, the location and size of the tumor, the particular compound used, its mode of administration, and the like. An appropriate amount may be determined by one of ordinary skill in the art using only routine experimentation given the teachings herein. Generally, dosage will preferably be in the range of about 0.5–500 mg/m$^2$, when considering 5'-methyl(talo)MeP-R for example, or a functional equivalent.

Depending on the intended mode of administration, the substrate can be in pharmaceutical compositions in the form of solid, semi-solid or liquid dosage forms, such as, for example, tablets, suppositories, pills, capsules, powders, liquids, or suspensions, preferably in unit dosage form suitable for single administration of a precise dosage. Time release preparations are specifically contemplated as effective dosage formulations. The compositions will include an effective amount of the selected substrate in combination with a pharmaceutically acceptable carrier and, in addition, may include other medicinal agents, pharmaceutical agents, carriers, or diluents.

For solid compositions, conventional nontoxic solid carriers include, for example, pharmaceutical grades of mannitol, lactose, starch, magnesium stearate, sodium saccharine, talc, cellulose, glucose, sucrose and magnesium carbonate. Liquid pharmaceutically administrable compositions can, for example, be prepared by dissolving or dispersing an active compound with optimal pharmaceutical adjuvants in an excipient, such as water, saline, aqueous dextrose, glycerol, or ethanol, to thereby form a solution or suspension. If desired, the pharmaceutical composition to be administered may also contain minor amounts of nontoxic auxiliary substances such as wetting or emulsifying agents, pH buffering agents, for example, sodium acetate or triethanolamine oleate. Actual methods of preparing such dosage forms are known, or will be apparent, to those skilled in this art; for example, see *Remington's Pharmaceutical Sciences*.

For oral administration, fine powders or granules may contain diluting, dispersing, and/or surface active agents, and may be presented in water or in a syrup, in capsules or sachets in the dry state or in a nonaqueous solution or suspension wherein suspending agents may be included, in tablets wherein binders and lubricants may be included, or in a suspension in water or a syrup. Where desirable or necessary, flavoring, preserving, suspending, thickening, or emulsifying agents may be included. Tablets and granules are preferred oral administration forms, and these may be coated.

Parenteral administration is generally by injection. Injectables can be prepared in conventional forms, either liquid solutions or suspensions, solid forms suitable for solution or prior to injection, or as suspension in liquid prior to injection or as emulsions.

The present invention provides a kit for impairing a cell that contains a vector containing a nucleotide sequence encoding an amino acid sequence depicted as SEQ ID No. 2 or a purified mutant PNP as depicted by SEQ ID No. 2 or a recombinant virus containing a nucleotide sequence encoding the mutant PNP depicted by SEQ ID No. 2. or any combination of these, together with instructions for use of the kit. The kit further includes any reagents or components necessary for the administration of the compounds.

The following examples are given for the purpose of illustrating various embodiments of the invention and are not meant to limit the present invention in any fashion.

EXAMPLE 1

Method for Identifying Candidate Prodrugs for Mutant PNP Enzymes

The following method is useful to identify substrates that are cleaved more efficiently by the mutant PNP than by wild-type PNP. Prodrugs identified by this method can then be further assessed by animal studies for determination of toxicity, suitability for administration with various pharmaceutical carriers, and other pharmacological properties.

The method quantitatively measures the cleavage of substrates in vitro. The purine analog nucleosides (0.1 mM) are incubated in 500 µl of 100 mM HEPES, pH 7.4, 50 mM potassium phosphate, and with 100 µg/ml mutant M65V *E. coli* PNP or wild-type PNP. The reaction mixtures are incubated at 25° C. for 1 hour, and the reactions stopped by boiling each sample for 2 minutes. Protein concentration and time of assay are varied depending on activity of an enzyme with a particular substrate. Each sample is analyzed by reverse phase HPLC to measure conversion from substrate to product. The nucleoside and purine analogs are eluted from a Spherisorb ODSI (5 µm) column (Keystone Scientific, Inc., State College, Pa.) with a solvent containing 50 mM ammonium dihydrogen phosphate (95%) and acetonitrile (5%) and products are detected by their absorbance at 254 nm, and are identified by comparing their retention times and absorption spectra with authentic samples.

By this analysis, mutant M65V PNP has more activity for 5'-methyl(talo)-MeP-R, 9-($\alpha$-L-lyxofuranosyl)-6-methylpurine and 9-($\alpha$-L-lyxofuranosyl)-adenine than the wild-type PNP. Thus, these substrates are preferred candidate prodrugs which are eligible for further assessment for use in the methods and compositions described herein to treat a pathological condition. Further, mutant M65A has more activity for 9-(6,7-dideoxy-$\alpha$-L-hept-6-ynofuranosyl)-6-methylpurine than does the wild-type enzyme indicating this substrate as preferable for use with this mutant.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

The invention claimed is:

1. A commercial kit comprising:
   a vector containing an isolated nucleotide sequence encoding an amino acid sequence comprising residues 1–239 of SEQ ID NO: 2; and
   instructions for use.

2. A commercial kit comprising:
   a recombinant virus containing an isolated nucleotide sequence encoding a mutant *E. coli* purine nucleoside phosphorylase protein comprising residues 1–239 of SEQ ID NO: 2; and
   instructions for use.

3. An isolated nucleotide sequence encoding a mutant *E. coli* purine nucleoside phosphorylase protein selected from the group consisting of: a mutant *E. coli* purine nucleoside phosphorylase protein having the amino acid sequence set forth in SEQ ID NO: 2 (M65V); isolated nucleotide sequence encoding a mutant *E. coli* purine nucleoside phosphorylase protein having the amino acid sequence set forth in SEQ ID NO: 4 (A157V); the mutant *E. coli* purine nucleoside phosphorylase protein having the amino acid sequence set forth in SEQ ID NO: 2 having a valine at position 65 and an alanine at position 157, wherein a methionine is substituted for the valine at position 65 and a leucine is substituted for the alanine at position 157 (A157L); the mutant *E. coli* purine nucleoside phosphorylase protein having the amino acid sequence set forth in SEQ ID NO: 2 having a valine at position 65 and a glutamic acid at position 180, wherein a methionine is substituted for the valine at position 65 and an aspartic acid is substituted for the glutamic acid at position 180 (E180D); and the mutant *E. coli* purine nucleoside phosphorylase protein having the amino acid sequence set forth in SEQ ID NO: 2 having a valine at position 65, wherein an alanine is substituted for the valine at position 65 (M65A).

4. A vector comprising the isolated nucleotide sequence of claim 3.

5. An isolated host cell transformed with a vector comprising the isolated nucleotide sequence of claim 3.

6. A recombinant virus which is capable of transferring a gene to a target cell and which comprises the isolated nucleotide sequence of claim 3.

7. An isolated host cell transformed with the virus of claim 6.

8. The isolated nucleotide sequence of claim 3 having the nucleotide sequence set forth in SEQ ID NO: 1.

9. The isolated nucleotide sequence of claim 3 having the nucleotide sequence set forth in SEQ ID No: 3.

* * * * *

SEQUENCE LISTING

<160> NUMBER OF SEQ ID NOS: 4

<210> SEQ ID NO 1
<211> LENGTH: 720
<212> TYPE: DNA
<213> ORGANISM: Escherichia coli

<400> SEQUENCE: 1

```
atggctaccc cacacattaa tgcagaaatg ggcgatttcg ctgacgtagt tttgatgcca      60
ggcgacccgc tgcgtgcgaa gtatattgct gaaactttcc ttgaagatgc ccgtgaagtg     120
```

```
aacaacgttc gcggtatgct gggcttcacc ggtacttaca aaggccgcaa aatttccgta    180
atgggtcacg gtgttggtat cccgtcctgc tccatctaca ccaaagaact gatcaccgat    240
ttcggcgtga agaaaattat ccgcgtgggt tcctgtggcg cagttctgcc gcacgtaaaa    300
ctgcgcgacg tcgttatcgg tatgggtgcc tgcaccgatt ccaaagttaa ccgcatccgt    360
tttaaagacc atgactttgc cgctatcgct gacttcgaca tggtgcgtaa cgcagtagat    420
gcagctaaag cactgggtat tgatgctcgc gtgggtaacc tgttctccgc tgacctgttc    480
tactctccgg acggcgaaat gttcgacgtg atggaaaaat acggcattct cggcgtggaa    540
atggaagcgg ctggtatcta cggcgtcgct gcagaatttg gcgcgaaagc cctgaccatc    600
tgcaccgtat ctgaccacat ccgcactcac gagcagacca ctgccgctga gcgtcagact    660
accttcaacg acatgatcaa aatcgcactg gaatccgttc tgctgggcga taaagagtaa    720
```

<210> SEQ ID NO 2
<211> LENGTH: 239
<212> TYPE: PRT
<213> ORGANISM: Escherichia coli

<400> SEQUENCE: 2

```
Met Ala Thr Pro His Ile Asn Ala Glu Met Gly Asp Phe Ala Asp Val
1               5                   10                  15

Val Leu Met Pro Gly Asp Pro Leu Arg Ala Lys Tyr Ile Ala Glu Thr
            20                  25                  30

Phe Leu Glu Asp Ala Arg Glu Val Asn Asn Val Arg Gly Met Leu Gly
        35                  40                  45

Phe Thr Gly Thr Tyr Lys Gly Arg Lys Ile Ser Val Met Gly His Gly
    50                  55                  60

Val Gly Ile Pro Ser Cys Ser Ile Tyr Thr Lys Glu Leu Ile Thr Asp
65                  70                  75                  80

Phe Gly Val Lys Lys Ile Ile Arg Val Gly Ser Cys Gly Ala Val Leu
                85                  90                  95

Pro His Val Lys Leu Arg Asp Val Val Ile Gly Met Gly Ala Cys Thr
            100                 105                 110

Asp Ser Lys Val Asn Arg Ile Arg Phe Lys Asp His Asp Phe Ala Ala
        115                 120                 125

Ile Ala Asp Phe Asp Met Val Arg Asn Ala Val Asp Ala Ala Lys Ala
    130                 135                 140

Leu Gly Ile Asp Ala Arg Val Gly Asn Leu Phe Ser Ala Asp Leu Phe
145                 150                 155                 160

Tyr Ser Pro Asp Gly Glu Met Phe Asp Val Met Glu Lys Tyr Gly Ile
                165                 170                 175

Leu Gly Val Glu Met Glu Ala Ala Gly Ile Tyr Gly Val Ala Ala Glu
            180                 185                 190

Phe Gly Ala Lys Ala Leu Thr Ile Cys Thr Val Ser Asp His Ile Arg
        195                 200                 205

Thr His Glu Gln Thr Thr Ala Ala Glu Arg Gln Thr Thr Phe Asn Asp
    210                 215                 220

Met Ile Lys Ile Ala Leu Glu Ser Val Leu Leu Gly Asp Lys Glu
225                 230                 235
```

<210> SEQ ID NO 3
<211> LENGTH: 720
<212> TYPE: DNA
<213> ORGANISM: Escherichia coli

<400> SEQUENCE: 3

```
atggctaccc cacacattaa tgcagaaatg ggcgatttcg ctgacgtagt tttgatgcca    60
ggcgacccgc tgcgtgcgaa gtatattgct gaaactttcc ttgaagatgc ccgtgaagtg   120
aacaacgttc gcggtatgct gggcttcacc ggtacttaca aaggccgcaa aatttccgta   180
atgggtcacg gtatgggtat cccgtcctgc tccatctaca ccaaagaact gatcaccgat   240
ttcggcgtga agaaaattat ccgcgtgggt tcctgtggcg cagttctgcc gcacgtaaaa   300
ctgcgcgacg tcgttatcgg tatgggtgcc tgcaccgatt ccaaagttaa ccgcatccgt   360
tttaaagacc atgactttgc cgctatcgct gacttcgaca tggtgcgtaa cgcagtagat   420
gcagctaaag cactgggtat tgatgctcgc gtgggtaacc tgttctccgt tgacctgttc   480
tactctccgg acggcgaaat gttcgacgtg atggaaaaat acggcattct cggcgtggaa   540
atggaagcgg ctggtatcta cggcgtcgct gcagaatttg gcgcgaaagc cctgaccatc   600
tgcaccgtat ctgaccacat ccgcactcac gagcagacca ctgccgctga gcgtcagact   660
accttcaacg acatgatcaa aatcgcactg gaatccgttc tgctgggcga taaagagtaa   720
```

<210> SEQ ID NO 4
<211> LENGTH: 239
<212> TYPE: PRT
<213> ORGANISM: Escherichia coli

<400> SEQUENCE: 4

```
Met Ala Thr Pro His Ile Asn Ala Glu Met Gly Asp Phe Ala Asp Val
1               5                   10                  15

Val Leu Met Pro Gly Asp Pro Leu Arg Ala Lys Tyr Ile Ala Glu Thr
            20                  25                  30

Phe Leu Glu Asp Ala Arg Glu Val Asn Asn Val Arg Gly Met Leu Gly
        35                  40                  45

Phe Thr Gly Thr Tyr Lys Gly Arg Lys Ile Ser Val Met Gly His Gly
    50                  55                  60

Met Gly Ile Pro Ser Cys Ser Ile Tyr Thr Lys Glu Leu Ile Thr Asp
65                  70                  75                  80

Phe Gly Val Lys Lys Ile Ile Arg Val Gly Ser Cys Gly Ala Val Leu
                85                  90                  95

Pro His Val Lys Leu Arg Asp Val Val Ile Gly Met Gly Ala Cys Thr
            100                 105                 110

Asp Ser Lys Val Asn Arg Ile Arg Phe Lys Asp His Asp Phe Ala Ala
        115                 120                 125

Ile Ala Asp Phe Asp Met Val Arg Asn Ala Val Asp Ala Ala Lys Ala
    130                 135                 140

Leu Gly Ile Asp Ala Arg Val Gly Asn Leu Phe Ser Val Asp Leu Phe
145                 150                 155                 160

Tyr Ser Pro Asp Gly Glu Met Phe Asp Val Met Glu Lys Tyr Gly Ile
                165                 170                 175

Leu Gly Val Glu Met Glu Ala Ala Gly Ile Tyr Gly Val Ala Ala Glu
            180                 185                 190

Phe Gly Ala Lys Ala Leu Thr Ile Cys Thr Val Ser Asp His Ile Arg
        195                 200                 205

Thr His Glu Gln Thr Thr Ala Ala Glu Arg Gln Thr Thr Phe Asn Asp
    210                 215                 220

Met Ile Lys Ile Ala Leu Glu Ser Val Leu Leu Gly Asp Lys Glu
225                 230                 235
```